United States Patent
Neumann et al.

(12)

(10) Patent No.: US 6,906,227 B2
(45) Date of Patent: Jun. 14, 2005

(54) BISPHENOL PHENOL ADDUCTS

(75) Inventors: Rainer Neumann, Krefeld (DE); Rolf Lanze, Krefeld (DE); Frieder Heydenreich, Düsseldorf (DE); Michael Bödiger, League City, TX (US); Michael Prein, Brasschaat (BE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/149,905

(22) PCT Filed: Dec. 7, 2000

(86) PCT No.: PCT/EP00/12323

§ 371 (c)(1),
(2), (4) Date: Sep. 5, 2002

(87) PCT Pub. No.: WO01/46105

PCT Pub. Date: Jun. 28, 2001

(65) Prior Publication Data

US 2003/0038094 A1 Feb. 27, 2003

(30) Foreign Application Priority Data

Dec. 20, 1999 (DE) .......................... 199 61 521

(51) Int. Cl.⁷ ................................. C07C 39/16
(52) U.S. Cl. ................. 568/724; 568/727; 568/728; 210/768; 210/772; 210/784; 210/402; 210/406
(58) Field of Search ................. 210/768, 772, 210/784, 402, 406; 568/724, 727, 728; 768/724, 727, 728

(56) References Cited

U.S. PATENT DOCUMENTS

| 3,972,950 A | * | 8/1976 | Kwantes ............... 568/724 |
| 4,212,997 A | * | 7/1980 | Adams et al. ......... 568/724 |
| 2003/0038094 A1 | * | 2/2003 | Neumann et al. ..... 210/768 |

FOREIGN PATENT DOCUMENTS

WO 94/19302 9/1994

* cited by examiner

Primary Examiner—Robert James Popovics
(74) Attorney, Agent, or Firm—Joseph C. Gil; Aron Preis

(57) ABSTRACT

The application relates to a process for producing high-purity bis(4-hydroxyaryl)alkanes from adducts of bis(4-hydroxyaryl)alkanes and aromatic hydroxy compounds, which are obtained by acid-catalysed reaction of the aromatic hydroxy compounds with ketones.

5 Claims, 1 Drawing Sheet

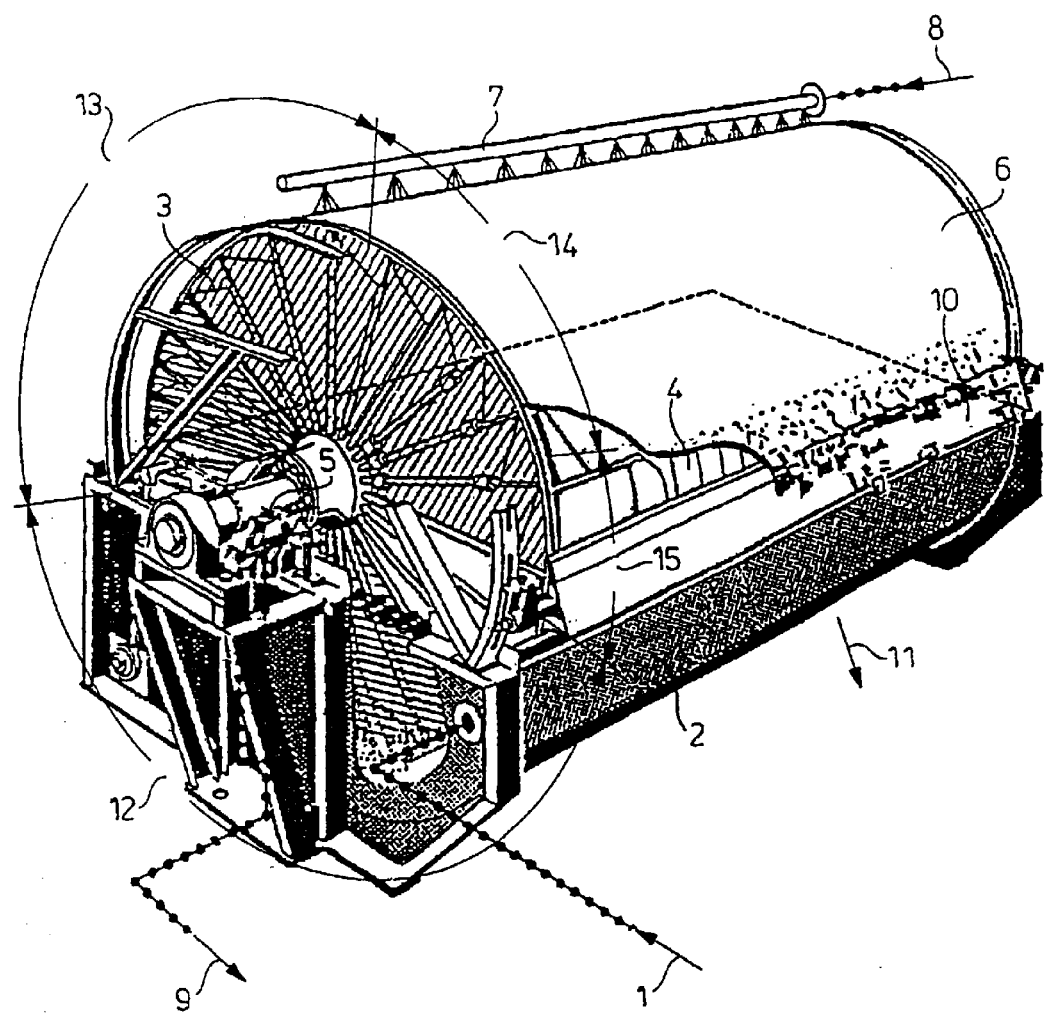

BISPHENOL PHENOL ADDUCTS

The present application relates to a process for producing high-purity bis(4-hydroxyaryl)alkanes from adducts of bis (4-hydroxyaryl)alkanes and aromatic hydroxy compounds, which are obtained by acid-catalysed reaction of the aromatic hydroxy compounds with ketones.

Bisphenols, as condensation products of phenols and carbonyl compounds, constitute starting materials or intermediate products for the production of a wide range of commercial products. Of particular industrial significance is the condensation product from the reaction between phenol and acetone, 2,2-bis(4-hydroxyphenyl)propane (BPA). BPA serves as the starting material for the production of various polymeric materials such as, for example, polyarylates, polyetherimides, polysulfones and modified phenol-formaldehyde resins. It is preferably used in the production of epoxy resins and polycarbonates.

Industrially relevant BPA production methods are known and are based on the acid-catalysed reaction of phenol and acetone, wherein a phenol-acetone ratio preferably greater than 5:1 is established in the reaction. The acid catalysts used may comprise both homogeneous and heterogeneous Brønsted or Lewis acids, such as for example strong mineral acids such as hydrochloric or sulfuric acid. Gel-form or macroporous sulfonated cross-linked polystyrene resins (acidic ion exchangers) are preferably used.

When phenol is reacted with acetone in the presence of acid catalysts, a product mixture arises which primarily contains BPA and water, in addition to unreacted phenol and optionally acetone. In addition typical condensation reaction by-products arise in small quantities, such as for example 2-(4-hydroxyphenyl)-2-(2-hydroxyphenyl)propane (o,p-BPA), substituted indenes, hydroxyphenyl indanols, hydroxyphenyl chromans, substituted xanthenes and more highly condensed compounds having three or more phenyl rings in the molecular framework.

The above-mentioned by-products, as well as water, phenol and acetone, impair the suitability of BPA for the production of polymers and have to be separated off by suitable processes. High purity levels are required of the raw material BPA in particular in the production of polycarbonate.

One method of working up and purifying BPA entails the separation of BPA from the reaction mixture in the form of an approximately equimolar crystalline adduct with phenol by cooling of the reaction mixture, with the BPA/phenol adduct being crystallised as a crystal suspension. The BPA/phenol adduct crystals are then separated from the liquid phase by a suitable apparatus for solid/liquid separation, such as a rotary filter or centrifuge, and fed to a further purification stage. The crystal mash leaving the crystallisers is passed to the rotary filters, for example, and is fed to the trough of the rotary filter, the rotary filter drum dipping into the crystal mash present therein.

The rotary filter drum is subdivided into different segments by means of a control head. The cake-forming zone, located in the area of the rotary filter trough, is adjoined by a washing zone, in which the filter cake is washed by spraying with phenol via rows of nozzles, followed by a drying zone, in which residual phenol contained in the filter cake is drawn off as far as possible. The cake-forming zone, washing zone and drying zone are each connected with the associated vacuum units.

After the drying zone, pressure equalisation is performed between suction chamber and rotary filter housing by means of a depressurisation zone in the control head, to allow problem-free detachment of the filter cake when it reaches the doctor blade. After removal of the filter cake, the filter cloth is washed with phenol via a row of nozzles before entry into the rotary filter trough.

To achieve an optimum, high-yield and high-purity process for producing BPA, separation of the BPA/phenol adduct crystals obtained by crystallisation from the mother liquor, which contains a large proportion of the impurities, and purification of the adduct crystals are crucial.

The object is to provide a process for optimum separation of the BPA/phenol adduct crystals from the mother liquor and purification of the crystals.

It has now been found that BPA is obtained effectively and economically by a special separation and purification process.

The following explanations relate substantially to the above-described BPA production processes.

The invention provides a process for separating and purifying adducts of bis(4-hydroxyaryl)alkanes and aromatic hydroxy compounds obtained during production by acid-catalysed reaction of aromatic hydroxy compounds with ketones, which process is characterised in that the adduct crystals formed in the process are separated from the mother liquor after crystallisation out of the suspension by continuous filtration in a revolving vacuum drum filter containing a plurality of filter cells and then washed, and the washing liquid is drawn off.

The invention preferably relates to the separation and purification of the 2,2-bis(4-hydroxyphenyl)propane/phenol adduct crystals (BPA/phenol adduct crystals) arising during production by acid-catalysed reaction of phenol and acetone.

Vacuum drum filters are known (e.g. Krauss Maffei drum filter TSF; FIG. 1). The drum filters preferably contain as filter cells a cake-forming zone (12), a washing zone (13), a drying suction zone (14), an aeration zone (15) and optionally a cake removal zone (10) and a cloth rinsing zone.

The BPA/phenol adduct crystal suspension arising during crystallisation passes into the vacuum drum filter via a feed stream. The solids content in the feed stream is preferably 5–35%, in particular 20–30%.

The feed stream preferably exhibits a temperature of from 40 to 70° C., in particular from 40 to 45° C., preferably around 41° C.

The quantity of adduct crystals separated from the suspension liquid as filter cake per unit time and per $m^2$ filter surface area is preferably 100 to 800 kg/h, in particular 300 to 700 kg/h.

A vacuum of from 5 to 500 mbar is preferably applied in the cake-forming zone.

A vacuum of from 5 to 300 mbar is preferably applied in the washing zone.

A vacuum of from 5 to 500 mbar is preferably applied in the drying suction zone.

Rinsing of the filter cake in the washing zone is performed with pure phenol at temperatures of preferably 45 to 70° C., in particular 50 to 60° C.

Filter cake cleaning is preferably performed using a rinsing agent quantity of 50–150% relative to the quantity of filter cake.

The washing or rinsing liquid is introduced via washing nozzles, preferably 10 to 30 washing nozzles. The nozzles are generally preferably so arranged that their spray cones overlap on the filter cake.

Cloth rinsing is preferably performed at temperatures of from 70 to 85° C., preferably 78 to 82° C., with pure phenol or with phenol recovered from the process by distillation.

Cloth rinsing is preferably performed using a rinsing agent quantity of from 20 to 100% relative to the amount of filter cake.

The filter cloth comprises a phenol- and heat-resistant filter cloth, preferably calendered once or twice, with air permeability of preferably 300 to 1500 l/dm$^2$/min, in particular 500 to 900 l/dm$^2$/min.

The rotary filter housing is preferably rendered inert with nitrogen under a slight excess pressure of 20 mbar, preferably 10 mbar. Nitrogen is preferably also passed through the washed filter cake. The nitrogen used preferably has an oxygen content of less than 1 ppm and is preferably recirculated, wherein approximately 3–10% of the recirculated quantity is preferably continuously discharged and replaced by pure nitrogen. The recirculated nitrogen is preferably washed with completely deionised water.

The drum rotation speed, filter cake thickness, recirculated nitrogen quantity and the suction openings in the control disk are set such that the residual moisture in the filter cake is below 30%, preferably 20%, in particular below 15%, relative to the mixed crystal quantity.

Drum roundness and scraper knife orientation are so set that the scraper knife is at a maximum distance from the drum of preferably 4–6 mm over the entire filter surface.

In a preferred embodiment, the BPA/phenol adduct crystals obtained in this way and separated and purified according to the invention are melted on a heating coil and, to keep the contact time between the adduct crystals and the hot stainless steel surface (1.4571) to a minimum, allowed to flow directly as a melt into a receiving tank.

The surface temperature of the heating coil is preferably 130 to 230° C., preferably 150 to 170° C. Melting is preferably performed under inert conditions, in particular with the exclusion of oxygen (oxygen content<1 ppm).

In FIG. 1, the reference numerals denote as follows:

1) mother liquor feed
2) trough
3) filter zone
4) filter cloth
5) control head
6) filter cake
7) washing nozzle
8) washing liquid
9) mother liquor outlet
10) doctor blade
11) solids
12) cake-forming zone
13) washing zone
14) drying zone
15) aeration zone The following Examples serve to explain the invention. The invention is not limited to the Examples. Where not otherwise indicated, percentages stand for percentages by weight.

EXAMPLE

Example 1

The BPA/phenol adduct crystals arising during the acid-catalysed reaction of phenol and acetone with subsequent suspension crystallisation are separated off from the liquid phase by a rotary filter and fed to further cleaning. To this end, a solids content in the feed stream of 25%, a feed temperature of 41° C. and a quantity of separated-off mixed crystals (filter cake) of 500 kg/h per m$^2$ of filter surface area are established.

Filtration is performed on a phenol- and heat-resistant filter cake (twice calendered) with air permeability of 700 l/dm$^2$/min. The vacuum in the cake-forming zone is 100 mbar, the vacuum in the washing zone is 80 mbar and the vacuum in the drying suction zone is 100 mbar. The rotary filter housing is rendered inert with nitrogen (<1 ppm oxygen) under a slight excess pressure of 10 mbar.

Drum rotation speed, filter cake thickness, recirculated nitrogen quantity (oxygen content<1 ppm) and the suction openings in the control disk are set such that the residual moisture in the filter cake is <15%, relative to the mixed crystal quantity. In addition, drum roundness and scraper knife orientation are so set that the scraper knife is at a maximum distance from the drum of approximately 5 mm over the entire filter surface.

Pure phenol at a temperature of 55° C. is used for rinsing the filter cake in the washing zone, wherein the rinsing agent quantity for filter cake purification is 100% relative to the filter cake quantity. For optimum filter cake washing, 20 washing nozzles are used, wherein the nozzles are so arranged that their spray cones overlap on the filter cake. Nitrogen (oxygen content<1 ppm) is passed through the washed filter cake, which nitrogen is recirculated, wherein approximately 7% of the recirculated quantity is continuously discharged and replaced by pure nitrogen and the recirculated nitrogen is washed with completely deionised water.

Directly after cake removal, the mixed crystals are melted on a heating coil under inert conditions (oxygen content<1 ppm), the melt flowing immediately to a receiving tank, to keep the contact time between the crystals and the hot stainless steel surface (1.4571) to a minimum. The surface temperature of the heating coil is approximately 160° C.

Phenol at a temperature of 80° C. is used for cloth rinsing, wherein the rinsing agent quantity for cloth rinsing is 80% relative to the quantity of filter cake.

A BPA/phenol adduct with high purity levels (>99% without phenol content) is obtained by this type of filtration.

What is claimed is:

1. A process for separating and purifying adducts of bis(4-hydroxyaryl)alkanes and aromatic hydroxy compounds obtained during production by acid-catalyzed reaction of aromatic hydroxy compounds with ketones, which process is characterized in that the adduct crystals formed in the process are separated from the mother liquor after crystallization out of the suspension by continuous filtration in a revolving vacuum drum filter containing a plurality of filter cells and then washed, and the washing liquid is drawn off, wherein the vacuum drum filter comprises a rotary filter housing and as filter cells a cake-forming zone, a washing zone, a drying suction zone, an aeration zone, a cake removal zone and a cloth rinsing zone, the vacuum applied in the cake-forming zone is 5 to 500 mbar, the vacuum applied in the washing zone is 5 to 300 mbar, the vacuum applied in the drying suction zone is 5 to 500 mbar, filter cake rinsing is performed in the washing zone using pure phenol at temperatures of 45 to 70° C. and using a rinsing agent quantity of 50 to 150 % relative to the quantity of filter cake, the filter cloth comprises a phenol- and heat-resistant filter cloth with air permeability of 300 to 1500 l/dm$^2$/min, and cloth rinsing is performed at temperatures of 70 to 85° C.

2. A process according to claim 1, characterised in that 2,2-bis(4-hydroxy-phenyl)propane/phenol adduct crystals (BPA/phenol adduct crystals) arising during acid-catalysed reaction of phenol and acetone are separated off and purified.

3. A process according to claim 1, characterised in that the quantity of adduct crystals separated from the suspension liquid as filter cake per unit time and per m$^2$ filter surface area is 100 to 800 kg/h.

4. A process according to claim 1, characterised in that the drum rotation speed, filter cake thickness, recirculated nitrogen quantity and the suction openings in the control disk are set such that the residual moisture in the filter cake is below 30%.

5. A process according to claim 1, characterised in that the purified BPA/phenol adduct crystals are melted on a heating coil and flow directly into a receiving tank as a melt.

* * * * *